United States Patent [19]

Romette et al.

[11] 4,235,687

[45] Nov. 25, 1980

[54] MEASURING CELL FOR MICRO-ASSAYS, COMPRISING MEMBRANE ELECTRODES

[75] Inventors: Jean-Louis Romette, Orrouy; Gerard Gellf, Compiegne; Daniel Thomas, Thourotte, all of France

[73] Assignee: Agence Nationale de Valorisation de la Recherche (ANVAR), Neuilly-sur-Seine (Anvar), France

[21] Appl. No.: 906,891

[22] Filed: May 16, 1978

[30] Foreign Application Priority Data

May 20, 1977 [FR] France ................................. 77 15615

[51] Int. Cl.³ .......................... G01N 27/30; C12Q 1/00
[52] U.S. Cl. ......................... 204/195 M; 204/195 B; 435/288; 435/291; 435/817
[58] Field of Search .................... 204/195 P, 1 P, 1 E, 204/195 B, 195 M; 195/127; 324/29, 30 R

[56] References Cited

U.S. PATENT DOCUMENTS

| | | | |
|---|---|---|---|
| 3,151,052 | 9/1964 | Arthur et al. | 204/195 F |
| 3,929,605 | 12/1975 | Lübbers et al. | 204/195 P |
| 3,997,420 | 12/1976 | Buzza | 204/195 P |
| 4,017,374 | 4/1977 | Aas et al. | 204/195 P |

OTHER PUBLICATIONS

R. A. Lienado et al., Anal. Chem., vol. 43, No. 11, pp. 1457–1461, (1971).

Michel Cordonnier et al., Febs Letters, vol. 59, No. 2, pp. 263–267, (1975).
Christian Calvot et al., Febs Letters, vol. 59, No. 2, pp. 258–262, (1975).
Anne–Marie Berjonneau et al., Pathologie–Biologie, vol. 22, No. 6, pp. 497–502, (1974).
G. G. Guilbault et al., Anal. Chem., vol. 42, No. 14, pp. 1779–1783, (1970).
S. J. Updike et al., Nature, vol. 214, 986–988, (1967).
G. G. Guilbault et al., J. Amer. Chem. Soc., vol. 91, 2164, (1969).

Primary Examiner—G. L. Kaplan
Attorney, Agent, or Firm—Sprung, Felfe, Horn, Lynch & Kramer

[57] ABSTRACT

The measuring cell is composed of at least one cavity hollowed in a block of chemically inert material or material made chemically inert at least at the surface. The cavity defines a first cylindrical space whose bottom is, over a reduced part of its diameter, extended by a second space defining the measuring chamber proper, of conical, frustoconical or substantially hemispherical shape. The first cylindrical space is designed to receive a measuring electrode terminated by a magnetic torus and, applied, and if necessary held by means of a ferromagnetic ring, against the latter, a membrane, while inlet and outlet ducts for the liquids to be assayed are formed in the block. The cell is especially useful for micro-assays of biological fluids.

14 Claims, 2 Drawing Figures

MEASURING CELL FOR MICRO-ASSAYS, COMPRISING MEMBRANE ELECTRODES

BACKGROUND OF THE INVENTION

1. Field of the Invention

The present invention relates to measuring cells adapted for micro-assays, notably for selective micro-assays of constituents in biological fluids, and comprising membrane electrodes. The invention also relates to an improved electrode carrying a membrane.

2. Description of the Prior Art

From the original studies of S. Updike and G. Kicks (Nature, Lond.—1967, 214, 986) is is known to be possible to assay selectively a substance in a heterogeneous biological fluid by using a conventional polarographic electrode (with a partial pressure of oxygen $pO_2$, for example) coated with a membrane bearing the specific enzyme of the substance to be assayed. Updike and Kicks have thus determined glucose with a $pO_2$ electrode coated with a polyacrylamide gel bearing glucoseoxydase included in the gel.

Since these initial studies, other investigations have been carried out, which have borne on the nature of the membranes, on the types of enzymes applicable and on the possibilities of utilizing different electrodes. In this respect, should be mentioned:

the article of G. G. Guilbault and J. Montalvo (J. Amer. Chem. Soc., 1969, 91, 2164) relating to determination of urea by a cation electrode equipped with an inclusion of urease in a polyacrylamide gel;

the article of G. G. Guilbault and E. Hrabankova (Analyt. Chem., 1970, 42,1779) relating to determination of total aminoacids by a $pO_2$ electrode equipped with an oxidase aminoacid inclusion and polyacrylamide;

French Pat. No. 1,604,982, as well as the first and second Certificates of Addition associated therewith, bearing respectively Nos. 69-01451 and 69-07897, wherein various modifications are described of a method for the preparation of enzymatic membranes having very much improved properties with respect to inclusions in the polyacrylamide; and the article of Berjonneau A. M., Thomas D. Broun G. (Path. Biol., 1974, 497, 502) entitled "Specific Assay of Aminoacids by $pCO_2$ Electrodes Equiped with Decarboxylase Membranes by Protein Coreticulation".

In addition, work carried out since 1969 by teams including the last-mentioned researchers have enabled full definition of the conditions of preparation of enzymatic membranes adapted for use with standard polarographic electrodes of various types, such as notably $pO_2$ and $pCO_2$ (see on this subject the article of Calvot C. et al in FEBS Letters, Vol. 59 No. 2, November 1975, pages 258–262 and the article of Cordonnier M. et al. in FEBS Letters, Vol. 59, No. 2, November 1975, pages 263–267).

Up to the present, these membranes have been used with commercial electrodes, for example electrodes of the type known under the tradename Radiometer; in such cases, the membrane is mounted on the sheath of the electrode by means of a toric seal of rubber. This method is delicate in assembly and, in addition, it causes mechanical stresses and irregular tension at the level of the membrane itself, so that it is impossible to avoid a notable percentage of torn membranes, as well as poor durability. Moreover, the size of the outer body of the electrode is then such that it is not possible to use an electrode of this design on microcells utilizing an overall volume of the analysis compartment of only 20 microliters.

In the article in Analytical Chemistry, Vol. 43, No. 11, September 1971, by R. A. Lienado et al, there is only described a measuring electrode bearing a membrane held in place by a cap of Plexiglas which includes a single cavity, without orifices for communication with the exterior, whilst an annular seal of rubber must be present to ensure fluid-tightness which is even then doubtful.

In the U.S. Pat. No. 3,151,052, an electrochemical cell of old design not including an enzymatic membrane, is described, and no suggestion is contained therein for utilizing such a membrane therewith.

It is an object of the present invention to provide an improved measuring cell for micro-assays comprising membrane electrodes, e.g. enzymatic membrane electrodes.

Other objects and advantages of the present invention will emerge from the description which follows.

GENERAL DESCRIPTION OF THE INVENTION

Applicants have now found that it is possible to carry out assays easily by utilizing a membrane, e.g. a membrane carrying specific enzymes, by means of a novel microcell according to the invention.

Applicants have also found that the placing in position of the measuring electrode is simplified, and that the operational safety of the latter is even increased, if the end of the electrode which is on the measuring side is adapted so as to position a magnetic torus there, that the membrane is applied against the latter and that it is held there by means of a suitable ferro-magnetic material.

According to the invention there is provided a cell, for assays utilizing membrane electrodes, essentially composed of at least one cavity hollowed out in a block of chemically inert material, or of material rendered chemically inert at least at the surface, so as to define a first cylindrical space whose bottom is, on a reduced part of its diameter, extended by a second space defining the measuring chamber proper, of conical, frustoconical or substantially hemispherical shape, said first cylindrical space being adapted to receive a measuring electrode therminated by a magnetic torus and, applied and if necessary held by means of a ferromagnetic ring against the latter, a membrane of circular shape cut out to the desired size, said possible ferromagnetic ring being supported on the bottom of said cylinder, whilst the ducts respectively for the inlet and the outlet of the liquids to be assayed and/or the passage of other fluids place in communication the periphery and/or the bottom of the cell with the measuring chamber, and open into the latter preferably substantially tangentially with respect to the surface of the membrane immobilized in said chamber.

The measuring cell according to this invention comprises ducts for the flow of the liquids to be assayed. These ducts, in practice two in number, preferably extend from the bottom of the block, in which the cavity is formed, to the measuring chamber part situated below the flat-bottomed cylindrical part of said cavity.

Advantageously the inlet and outlet ducts for the liquids have an inclination such that they open on the periphery of the measuring chamber, and substantially tangentially with respect to the surface of the membrane immobilized in said chamber. It has, in fact, been observed that this arrangement is the best if one wishes to avoid as far as possible the conventional risks of disturbing measurements by air bubbles on the membrane, and that it ensures good reproducibility of the measurements, and this even at the time of introducing samples of liquids including the constituent to be assayed, or rinsing solutions.

According to a further embodiment, the cell according to the invention comprises, in a single assembly, a plurality of measuring chambers such as defined above, each provided with its membrane electrode and mounted either in parallel or in series, the ducts respectively for inlet and/or for outlet being then connected together, in consequence.

According to yet another embodiment, the measuring cell according to the invention is equipped with two opposite electrodes such as described above, the measuring space then being, in a cavity obtained by drilling from side to side a block of chemically inert material or of material rendered chemically inert at least at the surface, bounded by said ferromagnetic ring suitably introduced or by a beading forming a cylindrical crown, ring or bead against which become flattened, on both sides, each of the two electrodes provided with membranes used, whilst the ducts respectively for the inlet and the outlet of the liquids to be assayed are arranged transversally, in opposition with respect to one another, and extending into said ferromagnetic ring or said bead, the two electrodes provided with their magnetic tori and their membranes being mounted directly on both sides of the latter and thus defining a single measuring cavity.

In practice, the block of material in which is formed the measuring cell according to the invention may be constituted of a plastics material, for example, of thermoplastics material, notably of polymethylmethacrylate, such as that known under the tradename Altuglas, or of any other chemically inert material, such as polymethyl (or ethyl) methacrylate or a polyacrylate, or of any material rendered chemically inert at least at the surface thereof.

According to a particularly advantageous embodiment, the cell according to the invention is formed in a block of metal, such as for example, stainless steel or any other metal or alloy, chemically inert or rendered chemically inert.

The ferromagnetic ring must itself also be chemically inert; it may be so either by its own nature, or by means of a suitable surface coating.

The ferromagnetic material may also be constituted by the cell itself or by at least the surface itself of the flat bottom of the cylindrical part of the abovesaid cavity.

The measuring cell according to the invention may in practice, according to any one of these embodiments, constitute a microcell for measuring in flow, liquids including constituents to be assayed. It is possible to adjust at will, by giving suitable dimensions to the abovesaid cavity, the measuring chamber, and to give the latter a final volume which may be as little as about 20 microliters.

In practice, the ferromagnetic ring, when such is provided, may be fixed, notably by gluing or by welding, if the respective materials allow it, on the flat bottom of the cylindrical part of the cavity formed in the block composing the measuring cell.

According to a most particularly advantageous embodiment of the measuring cell according to the invention, the cell comprises, in the immediate extension of the cylindrical part of said cavity and at the upper end, or free end, of the latter, an annular excrescence of an acute angle, suitable for stamping directly to the desired size discs of enzymatic membrane. This excrescence can be fastened, notably by gluing or by welding, on the measuring block, but it preferably forms a part of the latter, which has therefore been simply cut accordingly.

For its practical utilization, the measuring cell according to the invention can be thermostated, for example by immersion, in a bath or in an enclosure, of the cell-electrode assembly; in this case, a sleeve for access to the electrode or electrodes, is provided at the corresponding part of the enclosure and in the desired position.

As concerns the membrane itself, it will be understood that it could be of any kind, since the invention in no way depends on a special type of membrane. However typical membranes which may be used in the cell of this invention are enzymatic membranes, and notably an enzymatic membrane based on gelatine obtained by the process described in French Patent Application No. 77,15,616 of May 20, 1977 entitled "Process for Obtaining Biochemically Active Films and Coatings and Products Produced Thereby" to which reference may usefully be made.

As an illustrative, but in no way limiting, example of the application of the present invention, an improved electrode for assay cells with enzymatic membrane is used. Said electrode comprises an outer sheet adapted or tailored so as to receive, by simple stamping, a magnetic torus, on which the enzymatic membrane becomes applied.

It is thus possible to mount the enzymatic membrane easily by simple application of the latter at the level of said magnetic torus. The membrane is fixed either by simple application against the magnetic torus, if it is itself loaded with ferrite, or by gripping between the magnetic torus borne by the electrode and a ferromagnetic ring applied to the outer surface of said membrane, facing the magnetic torus.

The measuring cell according to the invention is especially, but not exclusively, suitable for selective assays in complex liquids by enzymatic membrane electrodes. It is, in particular, adapted for selective microassays of constituents in biological fluids, such as serum, urine, etc . . . , by means of enzymatic membrane electrodes.

DESCRIPTION OF A PREFERRED EMBODIMENT

Figure 1:
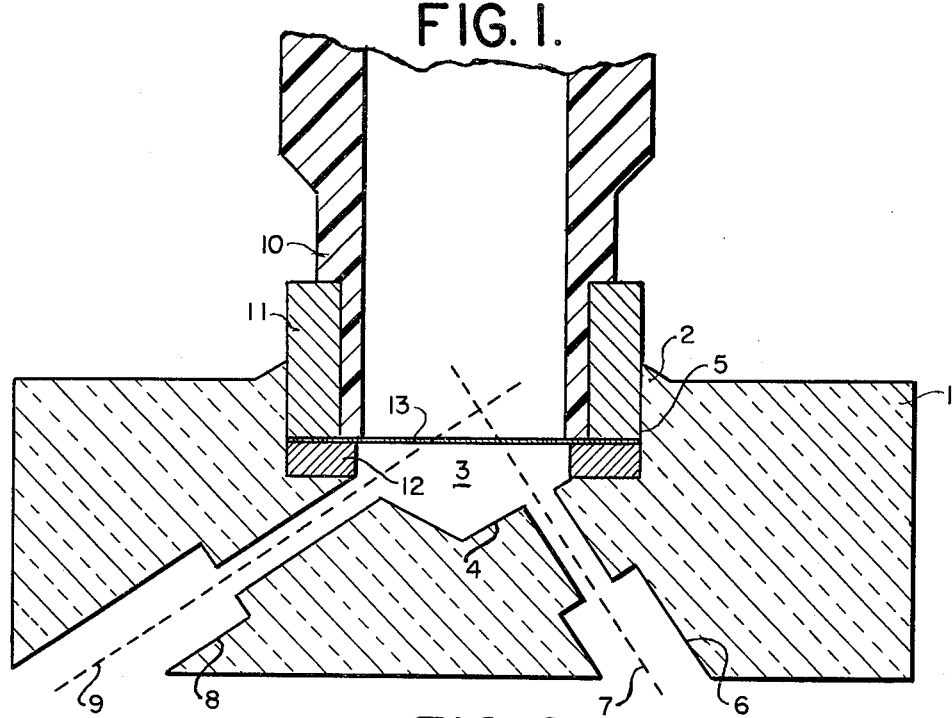
Figure 2:
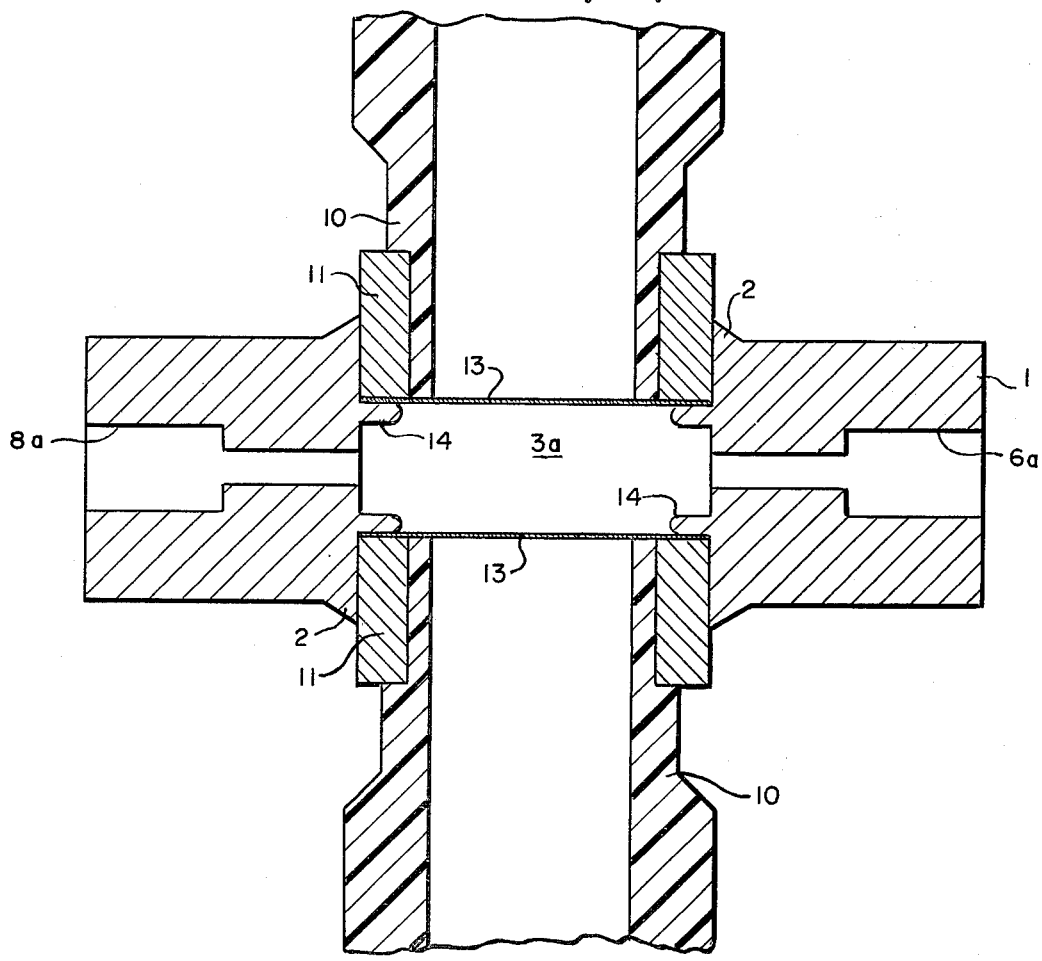

A preferred embodiment of a measuring cell for micro-assays according to the invention will now be described in more detail, with reference to the single accompanying drawing, wherein FIGS. 1 and 2 show two embodiments of measuring cells for micro-assays, provided with an enzymatic membrane electrode, according to the present invention and in transverse section.

These embodiments are, of course, purely illustrative and should not be regarded as limiting the invention in any way.

The cell in FIG. 1 comprises fundamentally a block 1 of Altuglas essentially constituted by a cylinder of 29 mm diameter and 10 mm height, except for an annular excrescence of acute angle 2 of about 0.7–1.0 mm in height and 11.8 mm internal diameter, corresponding strictly to the orifice of a cavity 3 formed in the block 1. The cavity 3 comprises a conical part 4 and a cylindrical part 5 with a flat bottom open on the conical part. This flat-bottomed cylindrical part has a diameter of 11.8 mm and a height of about 2.5 mm –3 mm. Two ducts are pierced in the Altuglas block, between the bottom of the latter and the conical part 4 of the cavity 3. The first of these ducts, or inlet duct 6 for liquids to be assayed, is directed along the axis 7 and comprises a first cylindrical part of 3.0 mm diameter, and a second cylindrical part of 1.0 mm diameter; these two parts each correspond substantially to half the length of the inlet duct 6. The second of these two ducts, or outlet duct 8 for the liquids to be assayed, is directed along the axis 9 and comprises, also in the direction going from the bottom of the block 1 to the cavity 3, a first cylindrical part of 3.00 mm diameter and a second cylindrical part of 1.0 mm diameter, each corresponding substantially to half the length of the outlet duct 8.

The measuring electrode becomes housed exactly in the cylindrical part 5 of the cavity 3: it comprises an electrode body 10, whose end, of plastic material, of internal diameter 6.6 mm, has been recut so as to have an external diameter of 7.8 mm over the height of 5.0 mm from this end. On this recut part is stamped hard a magnetic torus 11 having a height of 5.0 mm and internal and external diameters respectively of 7.8 mm and 11.8 mm. On its insertion into the cavity 3, previously equiped on the bottom of its cylindrical part 5 with a ferromagnetic ring 12, having a height of 1.0 mm and internal and external diameters respectively of 7.0 mm and 11.8 mm, the electrode body 10 provides with its magnetic torus 11 results, by cutting out in cooperation with the abovesaid annular excrescence 2, from a sheet-form enzymatic membrane applied on the top of the block 1, a disc 13 of enzymatic membrane of 11.8 mm diameter, which is held directly, without having to manipulate it in any way, between the magnetic torus 11 and the ferromagnetic ring 12.

As a modification, the cell was made, according to substantially the same specifications, in a block of stainless steel. It was thus possible to dispense with the insertion of a ferromagnetic ring and the substantially tangential arrangement of the ducts with respect to the membrane had thus been able to be better respected.

In FIG. 2 there is shown another measuring cell with two electrodes, like elements bearing the same reference numerals as in FIG. 1. In this embodiment the cavity is identified as 3a and is of cylindrical shape, being defined by the space between two membranes held in position between respective magnetic tori 11 and annular beads 14. The inlet and outlet ducts join up with the cavity from the sides because of the different configuration.

Various modifications of the measuring cell of the invention may be made without departing from the spirit or scope thereof and it is to be understood that the invention is to be limited only as defined in the appended claims.

We claim:

1. Measuring cell for assays utilizing membranes, said cell being essentially composed of at least one cavity hollowed out in a block of material, so as to define a first cylindrical space whose bottom is, over a reduced part of its diameter, extended by a second space defining the measuring chamber proper, of conical, frustoconical or substantially hemispherical shape, a measuring electrode terminated by a magnetic torus within said first cylindrical space, means holding the torus in position, a non-magnetic membrane of circular shape cut out to the desired size within said cavity adjacent the magnetic torus and between the end of said torus and the mating surface of the cavity, and ducts respectively for the inlet and outlet of the liquids to be assayed and/or the passage of other fluids connecting the periphery and/or the bottom of the cell with the measuring chamber, and open into the latter.

2. Measuring cell according to claim 1, wherein said ducts open into said measuring chamber substantially tangentially with respect to the surface of the membrane immobilized in said chamber.

3. Measuring cell according to claim 1, wherein the inlet and outlet ducts for the liquids to be assayed have an inclination such that they open on to the periphery of the measuring chamber.

4. Measuring cell according to claim 1, equipped with two opposite electrodes, the measuring space then being, in a cavity obtained by drilling said block of material from side-to-side, bounded by a ferromagnetic ring suitably introduced, each of the two electrodes being provided with a membrane, while the ducts respectively for the inlet and outlet of the liquid to be assayed are arranged transversally, in opposition with respect to one another, and penetrating into said ferromagnetic ring, the two electrodes provided with their magnetic tori and with their membranes being mounted directly on both sides of the ferromagnetic ring and thus defining a single measuring cavity.

5. Measuring cell according to claim 1, wherein said membrane is an enzymatic membrane.

6. Measuring cell according to claim 1, produced in a block of metal or plastic.

7. Measuring cell according to claim 6, wherein said blocks is made of a polyacrylate.

8. Measuring cell according to claim 7, wherein said polyacrylate is polymethyl methacrylate or polyethyl methacrylate.

9. Measuring cell according to claim 6, wherein said block is made of a metal alloy.

10. Measuring cell according to claim 9, wherein said block is made of stainless steel.

11. Measuring cell according to claim 1, wherein a ferromagnetic ring constitutes the means holding the torus in position, said ferromagnetic material being constituted by the cell itself or by at least the surface of the flat bottom of the cylindrical part of the cavity.

12. Measuring cell according to claim 1, comprising, in immediate extension of the cylindrical part of said cavity and at the upper end or free end of the latter, an annular excrescence of an acute angle, suitable for directly stamping out membrane discs of desired size from a larger sheet.

13. Measuring cell according to claim 1, wherein the means holding the torus in position comprises a ferromagnetic ring supported on the bottom of the cylinder within the cavity, the membrane being held between the torus and ring.

14. Measuring cell according to claim 1, equipped with two opposite electrodes, the measuring space then being, in a cavity obtained by drilling said block of material from side-to-side, bounded by a cylindrical crown, ring or bead flattened on both sides, each of the two electrodes being provided with a membrane, while the ducts respectively for the inlet and outlet of the liquids to be assayed are arranged transversally, in opposition with one another, and penetrating into said crown, ring or bead, the two electrodes provided with their magnetic tori and with their membranes being mounted directly on both sides of the crown, ring or bead and thus defining a single measuring cavity.

* * * * *